(12) United States Patent
Watanabe et al.

(10) Patent No.: US 11,846,407 B2
(45) Date of Patent: Dec. 19, 2023

(54) BARE OPTICAL FIBER MANUFACTURING METHOD

(71) Applicant: FURUKAWA ELECTRIC CO., LTD., Tokyo (JP)

(72) Inventors: Zyunpei Watanabe, Tokyo (JP); Hiroki Tanaka, Tokyo (JP); Kenichi Suyama, Tokyo (JP); Yoshihiro Arashitani, Tokyo (JP)

(73) Assignee: FURUKAWA ELECTRIC CO., LTD., Tokyo (JP)

( * ) Notice: Subject to any disclaimer, the term of this patent is extended or adjusted under 35 U.S.C. 154(b) by 142 days.

(21) Appl. No.: 17/324,645

(22) Filed: May 19, 2021

(65) Prior Publication Data

US 2021/0270448 A1 Sep. 2, 2021

Related U.S. Application Data

(60) Division of application No. 16/001,985, filed on Jun. 7, 2018, now Pat. No. 11,073,258, which is a
(Continued)

(30) Foreign Application Priority Data

Dec. 25, 2015 (JP) ................................. 2015-254793

(51) Int. Cl.
*F21V 15/01* (2006.01)
*C03C 25/12* (2006.01)
(Continued)

(52) U.S. Cl.
CPC ................ *F21V 15/01* (2013.01); *B05C 9/14* (2013.01); *B29C 33/06* (2013.01);
(Continued)

(58) Field of Classification Search
CPC ... B29C 2035/0827; B29C 35/10; B05D 3/06; F27D 11/12; C03C 25/12; C03C 25/10; C03C 25/6226; F21V 8/00; F21V 15/01
See application file for complete search history.

(56) References Cited

U.S. PATENT DOCUMENTS

| 5,128,175 A | 7/1992 | Yamanishi et al. |
| 5,219,623 A | 6/1993 | Petisce |

(Continued)

FOREIGN PATENT DOCUMENTS

| CN | 1193745 | 9/1998 |
| CN | 103319100 | 9/2013 |

(Continued)

OTHER PUBLICATIONS

European Office Action dated Aug. 19, 2022 in European Patent Application No. 16 878 968.3, 4 pages.

(Continued)

*Primary Examiner* — Karl Kurple
(74) *Attorney, Agent, or Firm* — Oblon, McClelland, Maier & Neustadt, L.L.P.

(57) ABSTRACT

A bare optical fiber manufacturing method includes applying an ultraviolet curable resin applied around an optical fiber; and irradiating the ultraviolet curable resin with ultraviolet light emitted from semiconductor ultraviolet light emitting elements, by use of an ultraviolet irradiation device having plural ultraviolet irradiation units each having plural positions where the ultraviolet light is emitted toward the ultraviolet curable resin, the plural positions being arranged on the same circle, the plural ultraviolet irradiation units being arranged in a traveling direction of the optical fiber such that the optical fiber passes centers of the circles, at least two of the plural ultraviolet irradiation units being differently arranged with respect to circumferential direction (Continued)

angles thereof around an axis that is the traveling direction of the optical fiber.

2 Claims, 10 Drawing Sheets

Related U.S. Application Data continuation of application No. PCT/JP2016/088486, filed on Dec. 22, 2016.

(51) Int. Cl.

| | | |
|---|---|---|
| *C23C 16/54* | (2006.01) | |
| *C03C 25/6226* | (2018.01) | |
| *H05B 45/10* | (2020.01) | |
| *B29C 33/06* | (2006.01) | |
| *H05B 1/02* | (2006.01) | |
| *B29C 35/08* | (2006.01) | |
| *B05C 9/14* | (2006.01) | |
| *B29C 35/10* | (2006.01) | |
| *A61N 5/06* | (2006.01) | |
| *F21Y 105/18* | (2016.01) | |
| *F21Y 105/14* | (2016.01) | |
| *F21Y 105/12* | (2016.01) | |

(52) U.S. Cl.
CPC .......... *B29C 35/0888* (2013.01); *B29C 35/10* (2013.01); *C03C 25/12* (2013.01); *C03C 25/6226* (2013.01); *C23C 16/545* (2013.01); *H05B 1/023* (2013.01); *H05B 45/10* (2020.01); *A61N 2005/0652* (2013.01); *B29C 2035/0827* (2013.01); *B32B 2310/0831* (2013.01); *F21Y 2105/12* (2016.08); *F21Y 2105/14* (2016.08); *F21Y 2105/18* (2016.08)

(56) References Cited

U.S. PATENT DOCUMENTS

| | | | | |
|---|---|---|---|---|
| 5,636,307 A | * | 6/1997 | Cowen | G02B 6/4486 385/127 |
| 7,362,940 B2 | | 4/2008 | Song et al. | |
| 8,277,138 B2 | | 10/2012 | Wakalopulos | |
| 2005/0222295 A1 | | 10/2005 | Siegel | |
| 2006/0007290 A1 | * | 1/2006 | Oshima | B41J 11/00214 347/102 |
| 2007/0227194 A1 | | 10/2007 | Song et al. | |
| 2009/0160923 A1 | | 6/2009 | Custer | |
| 2010/0183821 A1 | | 7/2010 | Hartsuiker et al. | |
| 2011/0239709 A1 | | 10/2011 | Okada | |
| 2012/0315023 A1 | * | 12/2012 | Collins | B29C 35/10 392/422 |
| 2013/0052364 A1 | | 2/2013 | Hartsuiker et al. | |
| 2014/0097361 A1 | | 4/2014 | Hartsuiker et al. | |
| 2015/0191030 A1 | | 7/2015 | Veis | |
| 2015/0210087 A1 | | 7/2015 | Fukumoto et al. | |
| 2015/0210876 A1 | | 7/2015 | Amao | |
| 2016/0229734 A1 | | 8/2016 | Okada | |
| 2017/0105257 A1 | | 4/2017 | Yue et al. | |
| 2018/0105629 A1 | | 4/2018 | Tada et al. | |

FOREIGN PATENT DOCUMENTS

| | | | | |
|---|---|---|---|---|
| CN | 105084783 | * | 11/2015 | ............. C03C 25/10 |
| CN | 105299529 | | 2/2016 | |
| GB | 2491603 | | 8/2013 | |
| JP | 61-58840 | | 3/1986 | |
| JP | 63-130313 | | 6/1988 | |
| JP | 2010-117525 | | 5/2010 | |
| JP | 2010-117526 | | 5/2010 | |
| JP | 2010-117527 | | 5/2010 | |
| JP | 2010-117530 | | 5/2010 | |
| JP | 2010-117531 | | 5/2010 | |
| JP | 2014-142631 | | 8/2014 | |
| JP | 2016-4927 | | 1/2016 | |
| JP | 2016-147771 | | 8/2016 | |

OTHER PUBLICATIONS

International Search Report dated Mar. 14, 2017 in PCT/JP2016/088486, filed on Dec. 22, 2016 ( with English Translation).
Written Opinion dated Mar. 14, 2017 in PCT/JP2016/088486, filed on Dec. 22, 2016.
Chinese Office Action dated Jul. 3, 2020 in Chinese Application No. 201680074451.7 (with computer generated English translation).

* cited by examiner

BARE OPTICAL FIBER MANUFACTURING METHOD

CROSS REFERENCES TO RELATED APPLICATION(S)

This application is a divisional of U.S. patent application Ser. No. 16/001,985, filed on Jun. 7, 2018, which is a continuation of PCT international application Ser. No. PCT/JP2016/088486, filed on Dec. 22, 2016 which designates the United States, incorporated herein by reference, and which claims the benefit of priority from Japanese Patent Application No. 2015-254793, filed on Dec. 25, 2015, incorporated herein by reference.

BACKGROUND

1. Field of the Invention

The present disclosure relates to a bare optical fiber manufacturing method, and an ultraviolet irradiation device.

2. Description of the Related Art

Generally, optical fibers made of quartz glass and the like have coatings formed on outer circumferential surfaces of optical fibers thereof (also called glass optical fibers), each of which is formed of a core and a cladding. An optical fiber having a coating formed therearound is called a bare optical fiber.

In a bare optical fiber manufacturing method, a bare optical fiber is manufactured by drawing an optical fiber from an optical fiber preform that is heated in a drawing furnace. Then, an ultraviolet light curable resin is applied onto an outer circumferential surface of the optical fiber in a resin applying apparatus, also known as a dies, and irradiated with ultraviolet light in an ultraviolet irradiation device, thereby to form a coating on the outer circumferential surface of the optical fiber.

In the past, a high-pressure mercury lamp or a metal halide lamp has generally been used as an ultraviolet light source of an ultraviolet irradiation device in a bare optical fiber manufacturing process. However, use of a semiconductor ultraviolet light emitting element, such as a light emitting diode (UV-LED) or a laser diode (UV-LD), which emits ultraviolet light, as an ultraviolet light source to be used in an ultraviolet irradiation device, is under investigation, in order to reduce maintenance costs, replacement frequencies, and power consumption (see, for example, Patent Literature 1 to Patent Literature 5 listed below).

PATENT LITERATURES

Patent Literature 1: Japanese Unexamined Patent Application, Publication No. 2010-117525
Patent Literature 2: Japanese Unexamined Patent Application, Publication No. 2010-117526
Patent Literature 3: Japanese Unexamined Patent Application, Publication No. 2010-117527
Patent Literature 4: Japanese Unexamined Patent Application, Publication No. 2010-117530
Patent Literature 5: Japanese Unexamined Patent Application, Publication No. 2010-117531

However, since ultraviolet light emitted from a semiconductor ultraviolet light emitting element has a single wavelength or a wavelength bandwidth narrower than that of a conventional lamp, which may be unfavorable in that the resin is not fully cured. If the resin is not fully cured, the bare optical fiber may be stuck or adhered on an underlying turn of the bare optical fiber when wound around a bobbin. Alternatively, transmission characteristics may deteriorate due to waviness generated in the optical fiber or discoloration of a surface of the optical fiber.

SUMMARY

The present disclosure has been made in view of the above, and is directed to a bare optical fiber manufacturing method and an ultraviolet irradiation device that enable ultraviolet curable resin to be cured sufficiently even if ultraviolet light of a single wavelength or a narrow wavelength bandwidth is used.

According to a first aspect of the present invention, there is provided a bare optical fiber manufacturing method including applying an ultraviolet curable resin applied around an optical fiber; and irradiating the ultraviolet curable resin with ultraviolet light emitted from semiconductor ultraviolet light emitting elements, by use of an ultraviolet irradiation device having plural ultraviolet irradiation units each having plural positions where the ultraviolet light is emitted toward the ultraviolet curable resin, the plural positions being arranged on the same circle, the plural ultraviolet irradiation units being arranged in a traveling direction of the optical fiber such that the optical fiber passes centers of the circles, at least two of the plural ultraviolet irradiation units being differently arranged with respect to circumferential direction angles thereof around an axis that is the traveling direction of the optical fiber.

According to a second aspect of the present invention, there is provided an ultraviolet irradiation device that irradiates an ultraviolet curable resin applied around an optical fiber, with ultraviolet light emitted from semiconductor ultraviolet light emitting elements, and cures the ultraviolet curable resin. The ultraviolet irradiation device includes plural ultraviolet irradiation units having plural positions where the ultraviolet light is emitted toward the ultraviolet curable resin, the plural positions being arranged on the same circle, the plural ultraviolet irradiation units being arranged in a traveling direction of the optical fiber such that the optical fiber passes centers of the circles, wherein at least two of the plural ultraviolet irradiation units are differently arranged with respect to circumferential direction angles thereof around an axis that is the traveling direction of the optical fiber.

DETAILED DESCRIPTION

Hereinafter, with reference to the appended drawings, a bare optical fiber manufacturing method and an ultraviolet irradiation device, according to an embodiment of the present disclosure, will be described in detail. The present disclosure is not limited by the embodiment described below. Further, it needs to be noted that the drawings are schematic, relations among dimensions of elements, ratios among the elements, and the like may be different from the actual ones. Furthermore, there may be a portion having different dimensional relations and ratios among the drawings.

Figure 1:
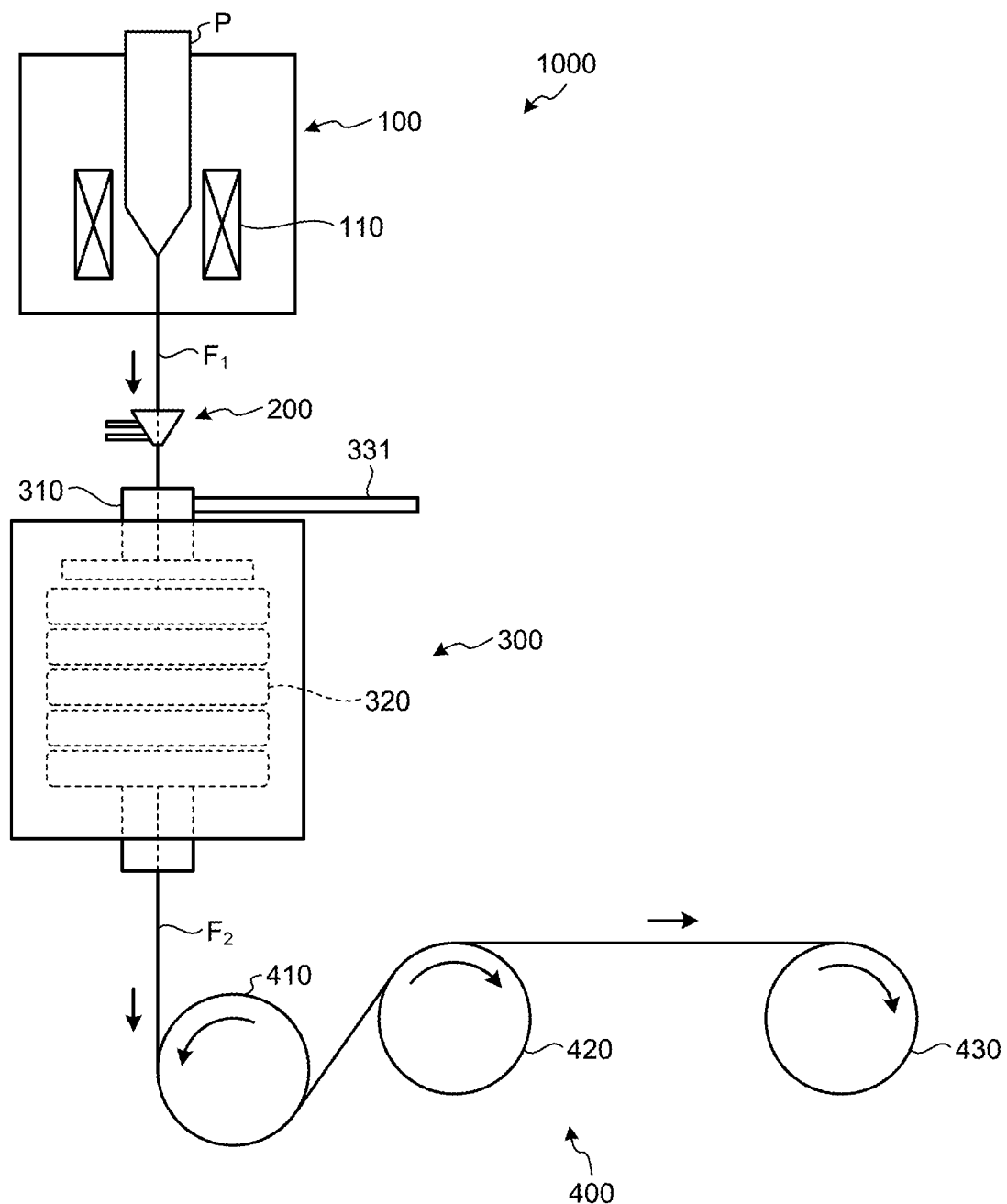
FIG. 1 is a schematic view illustrating an overall configuration of a bare optical fiber manufacturing apparatus used in a bare optical fiber manufacturing method according to an embodiment of the present disclosure.

FIG. 1 is a schematic view illustrating an overall configuration of a bare optical fiber manufacturing apparatus 1000 used in a bare optical fiber manufacturing method according to the embodiment of the present disclosure. As illustrated in FIG. 1, the bare optical fiber manufacturing apparatus 1000 includes a drawing furnace 100, a resin coating device 200, an ultraviolet irradiation device 300, and a winding device 400.

The drawing furnace 100 is for manufacturing an optical fiber $F_1$ from an optical fiber preform P, and includes a heater 110 for heating the optical fiber preform P. The optical fiber preform P is an intermediate product having an inner region that becomes a core in a final product and an outer region that becomes a cladding. The optical fiber $F_1$ is manufactured by drawing this optical fiber preform P so as to have a standardized outer diameter (for example, 125 µm).

The heater 110 included in the drawing furnace 100 heats a lower end of the optical fiber preform P to about 2000° C. The lower end of the optical fiber preform P that has been softened by the heating by the heater 110 is drawn by the winding device 400 provided downstream therefrom. Outer diameter of the optical fiber $F_1$ manufactured by the drawing furnace 100 is adjusted according to temperature of the heater 110, winding speed of the winding device 400, and the like.

The resin coating device 200 is a device that applies ultraviolet curable resin around the optical fiber $F_1$, and the ultraviolet irradiation device 300 is a device that cures the ultraviolet curable resin applied around the optical fiber $F_1$. Generally, at least two layers of coating, a primary (or inner) layer and a secondary (or outer) layer around the primary layer, are formed around the optical fiber $F_1$. A wet-on-wet method and a wet-on-dry method are known as methods of forming multiple layers of coating around the optical fiber $F_1$.

The wet-on-wet method is a method, in which plural ultraviolet curable resins are applied in plural layers onto the optical fiber $F_1$ in the resin coating device 200, and the plural layers of the ultraviolet curable resins are cured altogether or concurrently by ultraviolet irradiation in the ultraviolet irradiation device 300.

On the contrary, the wet-on-dry method is a method, in which plural stages each having a pair of the resin coating device 200 and the ultraviolet irradiation device 300 are provided, and coating is formed per layer by the resin coating device 200 and the ultraviolet irradiation device 300 of each of these stages.

Therefore, strictly speaking, the bare optical fiber manufacturing apparatus 1000 illustrated in FIG. 1 has an apparatus configuration of the wet-on-wet method. However, the embodiment of the present disclosure is not limited to the bare optical fiber manufacturing apparatus 1000 of the wet-on-wet method. Even if the bare optical fiber manufacturing apparatus 1000 is of the wet-on-dry method, the embodiment of the present disclosure is applicable to at least one of, or preferably all of, the plural stages each having the pair of the resin coating device 200 and the ultraviolet irradiation device 300. In order to avoid redundant descriptions, the embodiment of the present disclosure will be described herein by use of the configuration of the bare optical fiber manufacturing apparatus 1000 including only one pair of the resin coating device 200 and the ultraviolet irradiation device 300.

As illustrated in FIG. 1, the resin coating device 200 allows the optical fiber $F_1$ manufactured by the drawing furnace 100 to pass through an inside thereof. When the optical fiber $F_1$ passes inside the resin coating device 200, an ultraviolet curable resin for the primary layer, and/or an ultraviolet curable resin for the secondary layer are/is applied onto the optical fiber $F_1$.

The ultraviolet curable resin is, for example, a resin having at least two ethylenically unsaturated groups that are polymerized and cured by ultraviolet light, and preferably an oligomer is used as the ultraviolet curable resin. The oligomer is a polymer having a degree of polymerization of 2 to 100. Further, the ultraviolet curable resin has a photopolymerization initiator, for which examples will be described later, added therein.

Further, in addition to the oligomer and the photopolymerization initiator, the ultraviolet curable resin may contain any of, for example: a diluent monomer, a photosensitizer, a silane coupling agent, a chain transfer agent, and various additives. As the diluent monomer, a monofunctional (meth) acrylate or a polyfunctional (meth)acrylate is used. The diluent monomer means a monomer for dilution of the ultraviolet curable resin.

If a wavelength region of light emitted by a semiconductor ultraviolet light emitting element light source is 350 nm to 405 nm, the following may be used as the photopolymerization initiator having ultraviolet absorption in this wavelength region and capable of suitably curing a composition.

For example, the photopolymerization initiator may be any of: 2-methyl-1-[4-(methylthio)phenyl]-2-morpholino-propanone-1,2-benzyl-2-dimethylamino-1-(4-morpholino-phenyl)-butan-1-one; 2-(dimethylamino)-2-[(4-methylphe-nyl)methyl]-1-[4-(4-morpholinyl)phenyl]-1-butanone; N,N-dimethylaminoacetophenone, and the like, which are of the α-aminoketone type. Commercialized products thereof include Irgacure 907, Irgacure 369, Irgacure 379 (in trade names, manufactured by BASF Japan Co., Ltd.), and the like. "Irgacure" is a trademark of BASF Japan Co., Ltd.

Or, the photopolymerization initiator may be any of: 2,4,6-trimethylbenzoyldiphenylphosphine oxide; bis(2,4,6-trimethylbenzoyl)-phenylphosphine oxide; bis(2,6-dimethoxybenzoyl)-2,4,4-trimethyl-pentylphosphine oxide, and the like, which are of the acylphosphine oxide type. Commercialized products thereof include Irgacure 819, Lucirin TPO, Lucirin TPO-L, Irgacure 2100 (in trade names, manufactured by BASF Japan Co., Ltd.), and the like.

Or, the photopolymerization initiator may be any of: commercialized products, Irgacure OXE 01 and Irgacure OXE 02 (in trade names, manufactured by BASF Japan Co., Ltd.), which are of the O-acyloxime type.

As illustrated in FIG. 1, the ultraviolet irradiation device 300 allows the optical fiber to which the ultraviolet curable resin has been applied by the resin coating device 200, to pass an inside thereof. The optical fiber $F_1$ is irradiated with ultraviolet light when the optical fiber $F_1$ passes through the inside the ultraviolet irradiation device 300, and the ultraviolet curable resin applied thereon is cured.

The ultraviolet irradiation device 300 includes a transparent tube 310, plural ultraviolet irradiation units 320, and an inert gas introducing tube 331. The transparent tube 310 has transparency to ultraviolet light, and allows the optical fiber $F_1$ to travel along a central axis of the transparent tube 310 in a longitudinal direction thereof. Each of the ultraviolet irradiation units 320 has semiconductor ultraviolet light emitting elements that irradiate the optical fiber $F_1$ passing through the inside of the transparent tube 310, with ultraviolet light or deep ultraviolet light. As described as Examples later, any of plural types of configurations may be adopted as a configuration of the ultraviolet irradiation units 320 and the semiconductor ultraviolet light emitting elements.

Deep ultraviolet light is a part of ultraviolet light, and will be defined herein as follows. Ultraviolet light having wavelength of 365 nm to 405 nm will simply be referred to as ultraviolet light, and ultraviolet light having wavelength of 200 nm to 350 nm will be referred to as deep ultraviolet light. "Ultraviolet irradiation units 320" is a common name for plural ultraviolet irradiation units, and may include semiconductor ultraviolet light emitting elements that emit ultraviolet light, and/or semiconductor ultraviolet light emitting elements that emit deep ultraviolet light.

The inert gas introducing tube 331 is to fill the inside of the transparent tube 310 with inert gas. Generally, when ultraviolet curable resin is cured under an atmosphere with a relatively high concentration of oxygen ($O_2$), the ultraviolet curable resin reacts with oxygen and thus may be cured insufficiently. In order to prevent this, inert gas is supplied into the transparent tube 310 from the inert gas introducing tube 331, and the atmosphere inside the transparent tube 310 is decreased in oxygen concentration. As the inert gas, nitrogen ($N_2$) is typically used. However, the inert gas is not limited to $N_2$ as long as the inert gas is inert toward the optical fiber $F_1$ and the ultraviolet curable resin applied onto the optical fiber $F_1$.

The optical fiber $F_1$, in which the ultraviolet curable resin applied therearound has been cured by the ultraviolet irradiation device 300, is wound up as a bare optical fiber $F_2$, by the winding device 400. The winding device 400 includes guide rollers 410 and 420, and a winding drum 430. The winding device 400 illustrated in FIG. 1 is just an example, and the number and arrangement of rollers may be modified. As described already, by adjusting the speed, at which the winding device 400 winds up the bare optical fiber $F_2$, the winding device 400 controls the outer diameter of the optical fiber $F_1$ manufactured by the drawing furnace 100.

As described above, the bare optical fiber manufacturing apparatus 1000 illustrated in FIG. 1 is an apparatus that is able to manufacture the bare optical fiber $F_2$ by irradiating ultraviolet curable resin applied around the optical fiber $F_1$, with ultraviolet light emitted from the semiconductor ultraviolet light emitting elements, and curing the ultraviolet curable resin.

Hereinafter, examples of a configuration of ultraviolet irradiation units and semiconductor ultraviolet light emitting elements in an ultraviolet irradiation device will be described.

Example 1

Figure 2:
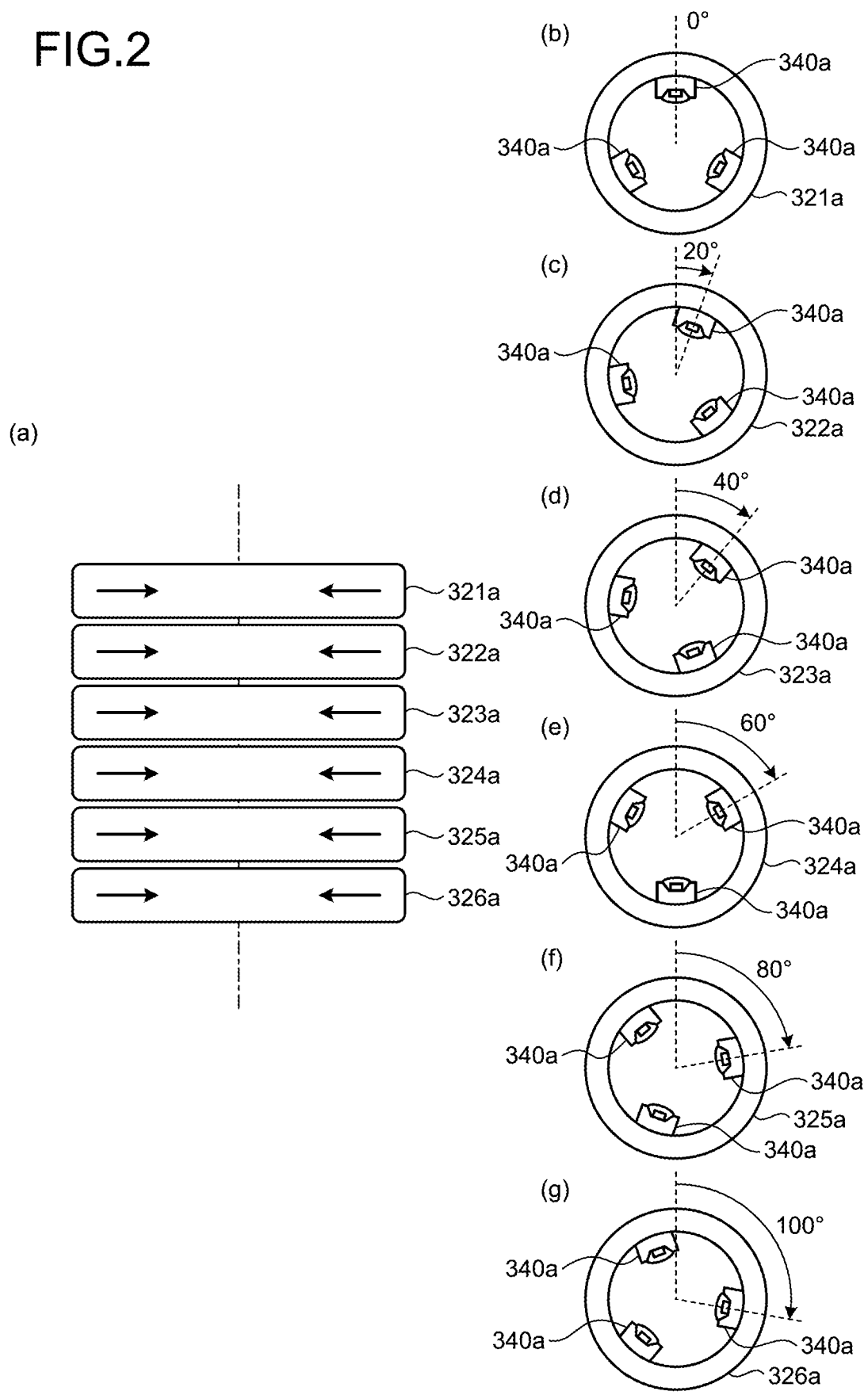
FIG. 2 is a diagram illustrating a configuration of ultraviolet irradiation units and semiconductor ultraviolet light emitting elements, according to Example 1.

FIG. 2 schematically illustrates ultraviolet irradiation units and semiconductor ultraviolet light emitting elements, according to Example 1. The ultraviolet irradiation units according to Example 1 are applicable as the plural ultraviolet irradiation units 320 in the above described ultraviolet irradiation device 300. Therefore, in order to avoid redundant explanations, only the configuration and arrangement of the ultraviolet irradiation units and semiconductor ultraviolet light emitting elements are illustrated in FIG. 2, and illustration of the other components is omitted.

As illustrated in FIG. 2, the ultraviolet irradiation units according to Example 1 includes first to sixth ultraviolet irradiation units 321a, 322a, 323a, 324a, 325a and 326a that irradiate ultraviolet curable resin with ultraviolet light. As illustrated in FIG. 2(b) to FIG. 2(g), the first to sixth ultraviolet irradiation units 321a to 326a are units of the same type, each unit having three semiconductor ultraviolet light emitting elements 340a arranged on the same circle, and as illustrated in FIG. 2(a), these first to sixth ultraviolet irradiation units 321a to 326a are arranged in a traveling direction of the optical fiber having the ultraviolet curable resin applied thereon such that the optical fiber passes the centers of the circles.

In FIG. 2(a), the optical fiber, though not illustrated, travels along a dashed line downwardly or in a direction from the ultraviolet irradiation units 321a through 326a. Further, since the optical fiber passes the centers of the circles on which the semiconductor ultraviolet light emitting elements 340a are arranged, the traveling position of the optical fiber coincides with a central axis of a cylindrical surface defined by arrangement positions of the semiconductor ultraviolet light emitting elements 340a.

As illustrated in FIG. 2(b) to FIG. 2(g), the first to sixth ultraviolet irradiation units 321a to 326a are arranged differently from one another in terms of an angle around the central axis that is the traveling direction of the optical fiber. Specifically, in relation to the first ultraviolet irradiation unit 321a, the second to sixth ultraviolet irradiation units 322a to 326a are rotationally deviated around the central axis respectively by 20°, 40°, 60°, 80°, and 100°.

Therefore, the semiconductor ultraviolet light emitting elements 340a included in the first to sixth ultraviolet irradiation units 321a to 326a are arranged in a spiral around the central axis that is the traveling direction of the optical fiber when the first to sixth ultraviolet irradiation units 321a to 326a are arranged in the traveling direction of the optical fiber. Further, the semiconductor ultraviolet light emitting elements 340a are arranged so as to be rotationally deviated from one another around the central axis, and a deviation angle between every two angularly adjacent semiconductor ultraviolet light emitting elements 340a is identical. As a result, the circumferential surface of the ultraviolet curable resin applied onto the optical fiber can be uniformly irradiated with the ultraviolet light, and formation of a satisfactory coating is enabled.

Arrows drawn in the first to sixth ultraviolet irradiation units 321a to 326a illustrated in FIG. 2(a) indicate emission directions of ultraviolet light emitted from the semiconductor ultraviolet light emitting elements 340a. That is, the semiconductor ultraviolet light emitting elements 340a included in the first to sixth ultraviolet irradiation units 321a to 326a emit ultraviolet light perpendicularly to the central axis representing the traveling direction of the optical fiber.

Example 2

Figure 3:
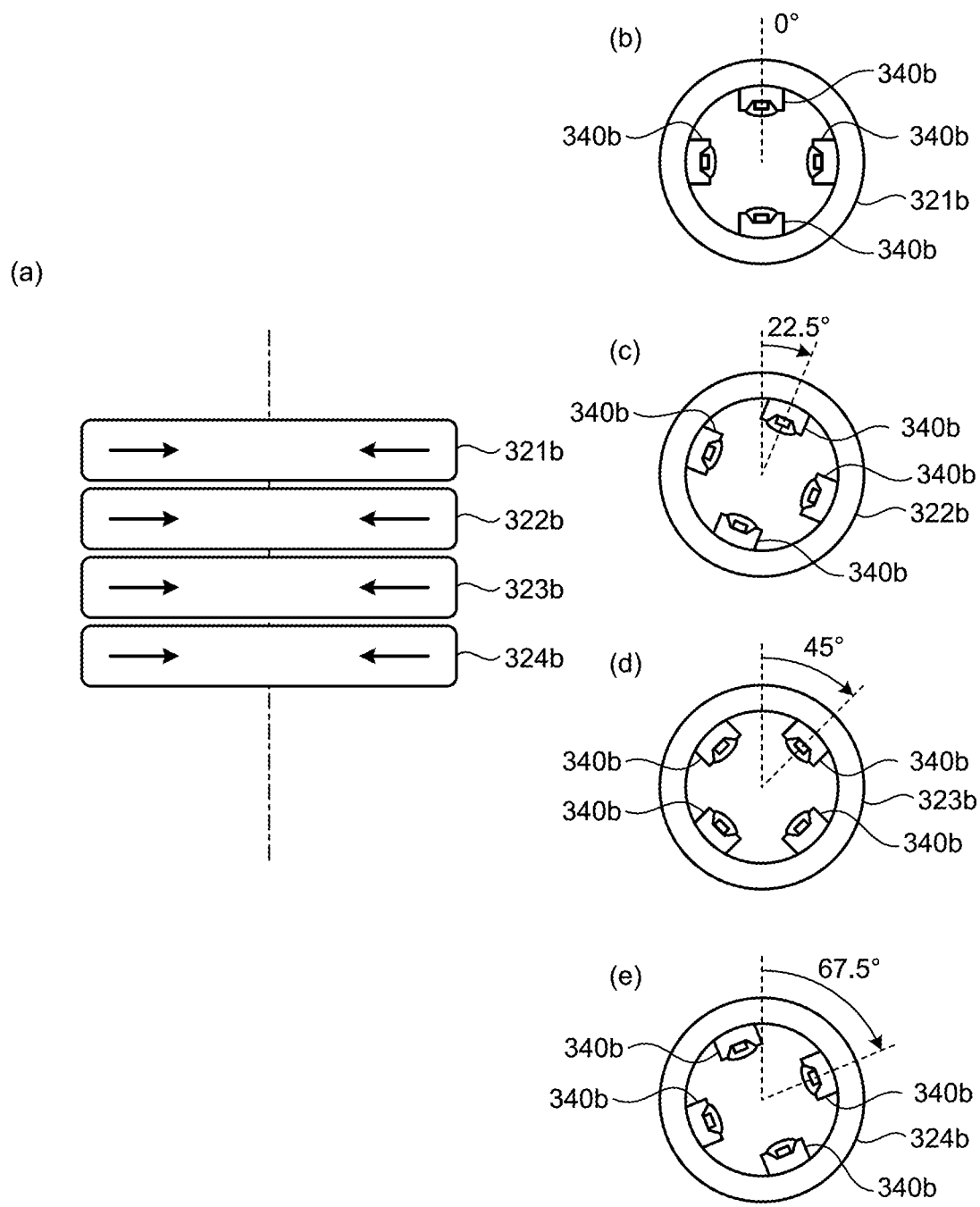
FIG. 3 is a diagram illustrating a configuration of ultraviolet irradiation units and semiconductor ultraviolet light emitting elements, according to Example 2.

FIG. 3 schematically illustrates ultraviolet irradiation units and semiconductor ultraviolet light emitting elements, according to Example 2. The ultraviolet irradiation units according to Example 2 are also applicable as the plural ultraviolet irradiation units 320 in the above described ultraviolet irradiation device 300.

As illustrated in FIG. 3, the ultraviolet irradiation units according to Example 2 include first to fourth ultraviolet irradiation units 321b, 322b, 323b and 324b that irradiate ultraviolet curable resin with ultraviolet light. As illustrated in FIG. 3(b) to FIG. 3(e), the first to fourth ultraviolet irradiation units 321b to 324b are units of the same type, each unit having four semiconductor ultraviolet light emitting elements 340b arranged on the same circle, and as illustrated in FIG. 3(a), these first to fourth ultraviolet irradiation units 321b to 324b are arranged in the traveling direction of an optical fiber such that the optical fiber passes the centers of the circles.

In FIG. 3(a), the optical fiber, though not illustrated, travels along a dashed line downwardly or in a direction from the ultraviolet irradiation units 321b through 324b. Further, since the optical fiber passes the centers of the circles on which the semiconductor ultraviolet light emitting elements 340b are arranged, the traveling position of the optical fiber coincides with a central axis of a cylindrical surface defined by arrangement positions of the semiconductor ultraviolet light emitting elements 340b.

As illustrated in FIG. 3(b) to FIG. 3(e), the first to fourth ultraviolet irradiation units 321b to 324b are arranged differently from one another in terms of an angle around the central axis that is the traveling direction of the optical fiber. Specifically, in relation to the first ultraviolet irradiation unit 321b, the second to fourth ultraviolet irradiation units 322b to 324b are rotationally deviated around the central axis respectively by 22.5°, 45°, and 67.5°.

Therefore, the semiconductor ultraviolet light emitting elements 340b included in the first to fourth ultraviolet irradiation units 321b to 324b are arranged in a spiral around the central axis that is the traveling direction of the optical fiber when the first to fourth ultraviolet irradiation units 321b to 324b are arranged in the traveling direction of the optical fiber. Further, the semiconductor ultraviolet light emitting elements 340b are arranged so as to be rotationally deviated from one another around the central axis, and a deviation angle between every two angularly adjacent semiconductor ultraviolet light emitting elements 340b is identical. As a result, the circumferential surface of the ultraviolet curable resin applied onto the optical fiber can be uniformly irradiated with the ultraviolet light, and formation of a satisfactory coating is enabled.

Arrows drawn in the first to fourth ultraviolet irradiation units 321b to 324b illustrated in FIG. 3(a) indicate emission directions of ultraviolet light emitted from the semiconductor ultraviolet light emitting elements 340b. That is, the semiconductor ultraviolet light emitting elements 340b included in the first to fourth ultraviolet irradiation units 321b to 324b emit ultraviolet light perpendicularly to the central axis representing the traveling direction of the optical fiber.

Example 3

Figure 4:
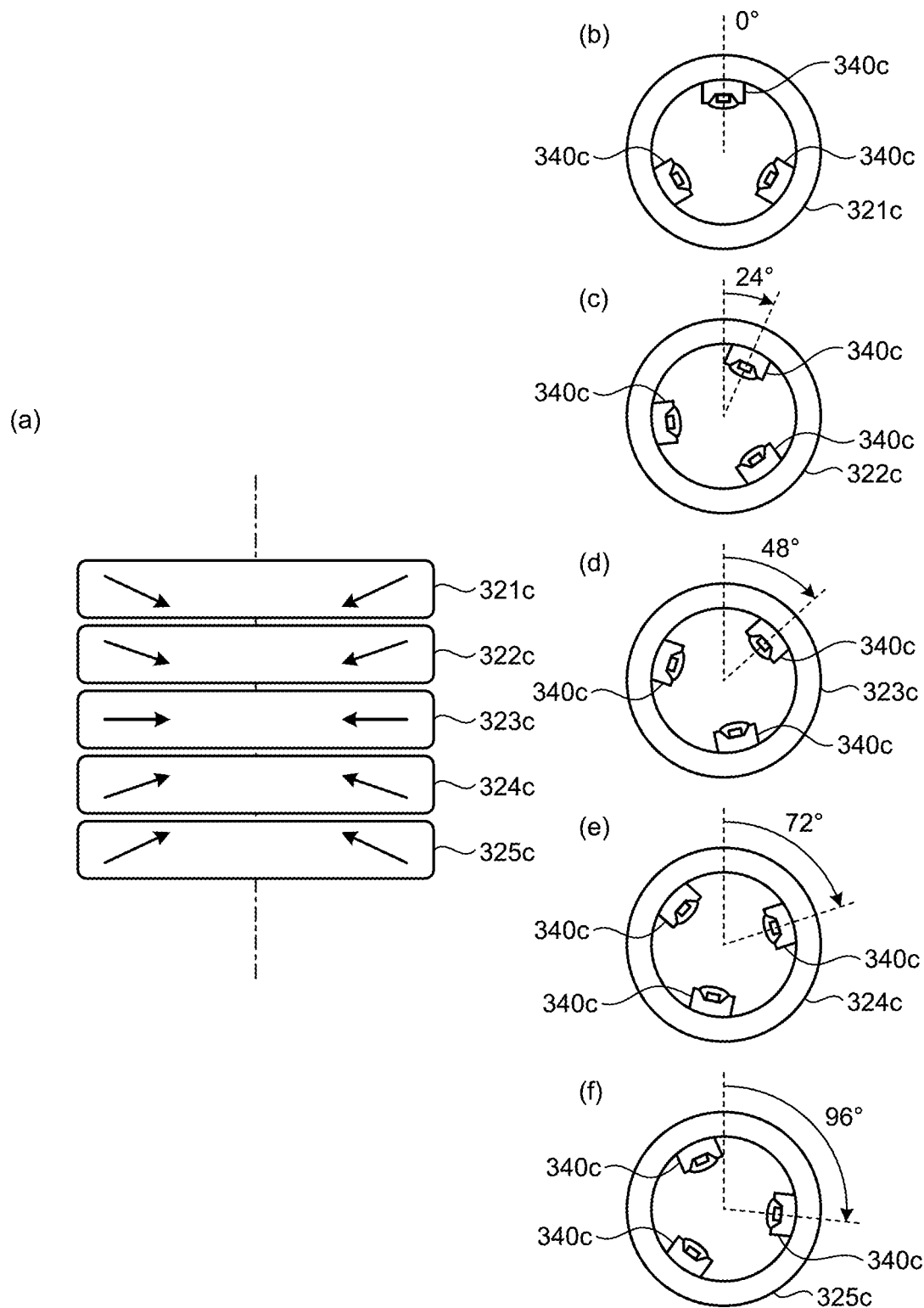
FIG. 4 is a diagram illustrating a configuration of ultraviolet irradiation units and semiconductor ultraviolet light emitting elements, according to Example 3.

FIG. 4 schematically illustrates ultraviolet irradiation units and semiconductor ultraviolet light emitting elements, according to Example 3. The ultraviolet irradiation units according to Example 3 are also applicable as the plural ultraviolet irradiation units 320 in the above described ultraviolet irradiation device 300.

As illustrated in FIG. 4, the ultraviolet irradiation units according to Example 3 include first to fifth ultraviolet irradiation units 321c, 322c, 323c, 324c, and 325c that irradiate ultraviolet curable resin with ultraviolet light. As illustrated in FIG. 4(b) to FIG. 4(f), the first to fifth ultraviolet irradiation units 321c to 325c are units of the same type, each unit having three semiconductor ultraviolet light emitting elements 340c arranged on the same circle, and as illustrated in FIG. 4(a), these first to fifth ultraviolet irradiation units 321c to 325c are arranged in the traveling direction of an optical fiber such that the optical fiber passes the centers of the circles.

In FIG. 4(a), the optical fiber, though not illustrated, travels along a dashed line downwardly or in a direction from the ultraviolet irradiation units 321c through 325c. Further, since the optical fiber passes the centers of the circles on which the semiconductor ultraviolet light emitting elements 340c are arranged, the traveling position of the optical fiber coincides with the central axis of a cylindrical surface defined by arrangement positions of the semiconductor ultraviolet light emitting elements 340c.

As illustrated in FIG. 4(b) to FIG. 4(f), the first to fifth ultraviolet irradiation units 321c to 325c are arranged differently from one another in terms of an angle around the central axis that is the traveling direction of the optical fiber. Specifically, in relation to the first ultraviolet irradiation unit 321c, the second to fifth ultraviolet irradiation units 322c to 325c are rotationally deviated around the central axis respectively by 24°, 48°, 72°, and 96°.

Therefore, the semiconductor ultraviolet light emitting elements 340c included in the first to fifth ultraviolet irradiation units 321c to 325c are arranged in a spiral around the central axis that is the traveling direction of the optical fiber when the first to fifth ultraviolet irradiation units 321c to 325c are arranged in the traveling direction of the optical fiber. Further, the semiconductor ultraviolet light emitting elements 340c are arranged so as to be rotationally deviated from one another around the central axis, and a deviation angle between every two angularly adjacent semiconductor ultraviolet light emitting elements 340c is identical. As a result, the circumferential surface of the ultraviolet curable resin applied onto the optical fiber can be uniformly irradiated with the ultraviolet light, and formation of a satisfactory coating is enabled.

Arrows drawn in the first to fifth ultraviolet irradiation units 321c to 325c illustrated in FIG. 4(a) indicate emission directions of ultraviolet light emitted from the semiconductor ultraviolet light emitting elements 340c. That is, the semiconductor ultraviolet light emitting elements 340c are installed in an inclined manner in the ultraviolet irradiation units 321c, 322c, 324c, and 325c so that the ultraviolet light is emitted from the ultraviolet irradiation units 321c to 325c toward the vicinity of a single point on the central axis representing the traveling direction of the optical fiber, as a whole. As will be described in detail with verification experiments later, by the inclined arrangement of these semiconductor ultraviolet light emitting elements 340c, illuminance of ultraviolet light emitted onto the ultraviolet curable resin is increased, and curing of the ultraviolet curable resin is promoted.

Example 4

Figure 5:
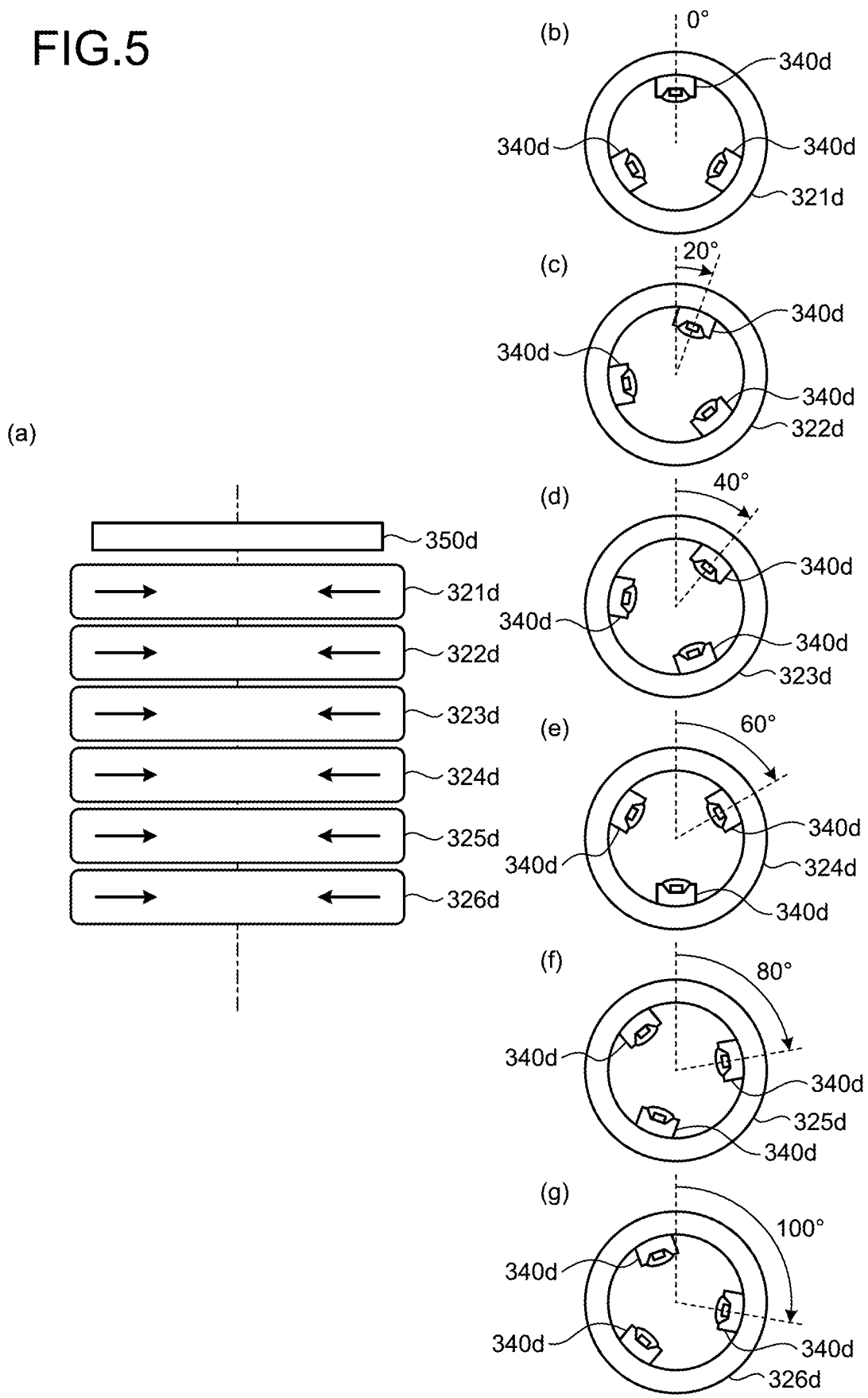
FIG. 5 is a diagram illustrating a configuration of ultraviolet irradiation units and semiconductor ultraviolet light emitting elements, according to Example 4.

FIG. 5 schematically illustrates ultraviolet irradiation units and semiconductor ultraviolet light emitting elements, according to Example 4. The ultraviolet irradiation units according to Example 4 are also applicable as the plural ultraviolet irradiation units 320 in the above described ultraviolet irradiation device 300.

As illustrated in FIG. 5, the ultraviolet irradiation units according to Example 4 included first to sixth ultraviolet irradiation units 321d, 322d, 323d, 324d, 325d, and 326d that irradiate ultraviolet curable resin with ultraviolet light and a deep ultraviolet irradiation unit 350d that emits deep ultraviolet light. As illustrated in FIG. 5(b) to FIG. 5(g), the first to sixth ultraviolet irradiation units 321d to 326d are units of the same type, each unit having three semiconductor ultraviolet light emitting elements 340d arranged on the same circle, and as illustrated in FIG. 5(a), these first to sixth ultraviolet irradiation units 321d to 326d are arranged in the traveling direction of the optical fiber such that the optical fiber passes the centers of the circles. Further, the deep ultraviolet irradiation unit 350d is arranged upstream of (upper than, on the plane of paper) the first ultraviolet irradiation unit 321d relative to the travelling direction of the optical fiber. The deep ultraviolet irradiation unit 350d has semiconductor ultraviolet light emitting elements provided therein, which emit deep ultraviolet light, and which are, for example, arranged similarly to those in the first ultraviolet irradiation unit 321d.

Deep ultraviolet light (for example, of wavelength of 200 nm to 350 nm) is shorter in wavelength than normal ultraviolet light (for example, of wavelength of 365 nm to 405 nm). The Deep ultraviolet light penetrates shallower into the ultraviolet curable resin than the normal ultraviolet light, and thus acts on a shallower part (or a superficial layer) of the ultraviolet curable resin. Therefore, the deep ultraviolet irradiation unit 350d is preferably arranged upstream of the first ultraviolet irradiation unit 321d, which leads to curing of ultraviolet curable resin in a layer closer to the surface, first. As described already, since ultraviolet curable resins react with oxygen and are not cured sufficiently when they are cured in an atmosphere high in oxygen concentration, by introduction of inert gas, ultraviolet curable resins are prevented from reacting with oxygen. Arranging the deep ultraviolet irradiation unit 350d upstream of the first ultraviolet irradiation unit 321d and curing first the ultraviolet curable resin in a layer closer to the surface that more easily reacts with oxygen contribute to improvement in quality of the surface.

The ultraviolet irradiation units according to Example 4 may be considered as units having the deep ultraviolet irradiation unit 350d in addition to the ultraviolet irradiation units according to Example 1. Therefore, the ultraviolet irradiation units according to Example 4 provide substantially the same functions and effects of the ultraviolet irradiation units according to Example 1.

Example 5

Figure 6:
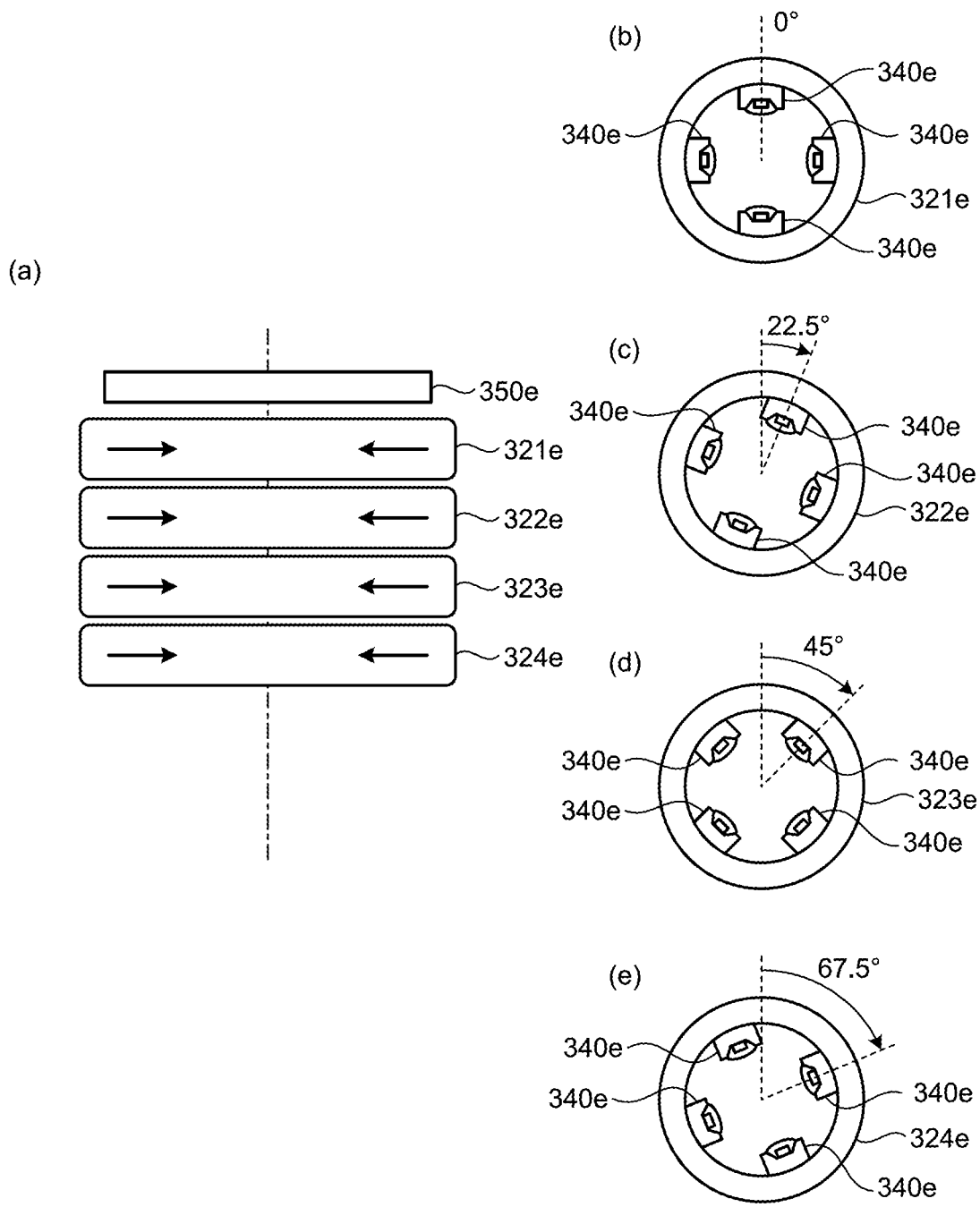
FIG. 6 is a diagram illustrating a configuration of ultraviolet irradiation units and semiconductor ultraviolet light emitting elements, according to Example 5.

FIG. 6 schematically illustrates ultraviolet irradiation units and semiconductor ultraviolet light emitting elements, according to Example 5. The ultraviolet irradiation units according to Example 5 are also applicable as the plural ultraviolet irradiation units 320 in the above described ultraviolet irradiation device 300.

As illustrated in FIG. 6, the ultraviolet irradiation units according to Example 5 include first to fourth ultraviolet irradiation units 321e, 322e, 323e, and 324e that irradiate ultraviolet curable resin with ultraviolet light, and a deep ultraviolet irradiation unit 350e that performs irradiation with deep ultraviolet light. As illustrated in FIG. 6(b) to FIG. 6(e), the first to fourth ultraviolet irradiation units 321e to 324e are units of the same type, each unit having four semiconductor ultraviolet light emitting elements 340e arranged on the same circle, and as illustrated in FIG. 6(a), these first to fourth ultraviolet irradiation units 321e to 324e are arranged in the traveling direction of the optical fiber such that the optical fiber passes the centers of the circles. Further, the deep ultraviolet irradiation unit 350e is arranged upstream of (upper than, on the plane of paper) the first ultraviolet irradiation unit 321e relative to the travelling direction of the optical fiber. The deep ultraviolet irradiation unit 350e has the same configuration as the deep ultraviolet irradiation unit 350d according to Example 4.

Similarly to Example 4, arrangement of the deep ultraviolet irradiation unit 350e upstream of the first ultraviolet irradiation unit 321e contributes to improvement in quality of the surface, through curing of ultraviolet curable resin in a layer closer to the surface that more easily reacts with oxygen, first.

The ultraviolet irradiation units according to Example 5 may be considered as units having the deep ultraviolet irradiation unit 350e in addition to the ultraviolet irradiation units according to Example 2. Therefore, the ultraviolet irradiation units according to Example 5 provide substantially the same functions and effects of the ultraviolet irradiation units according to Example 2.

Example 6

Figure 7:
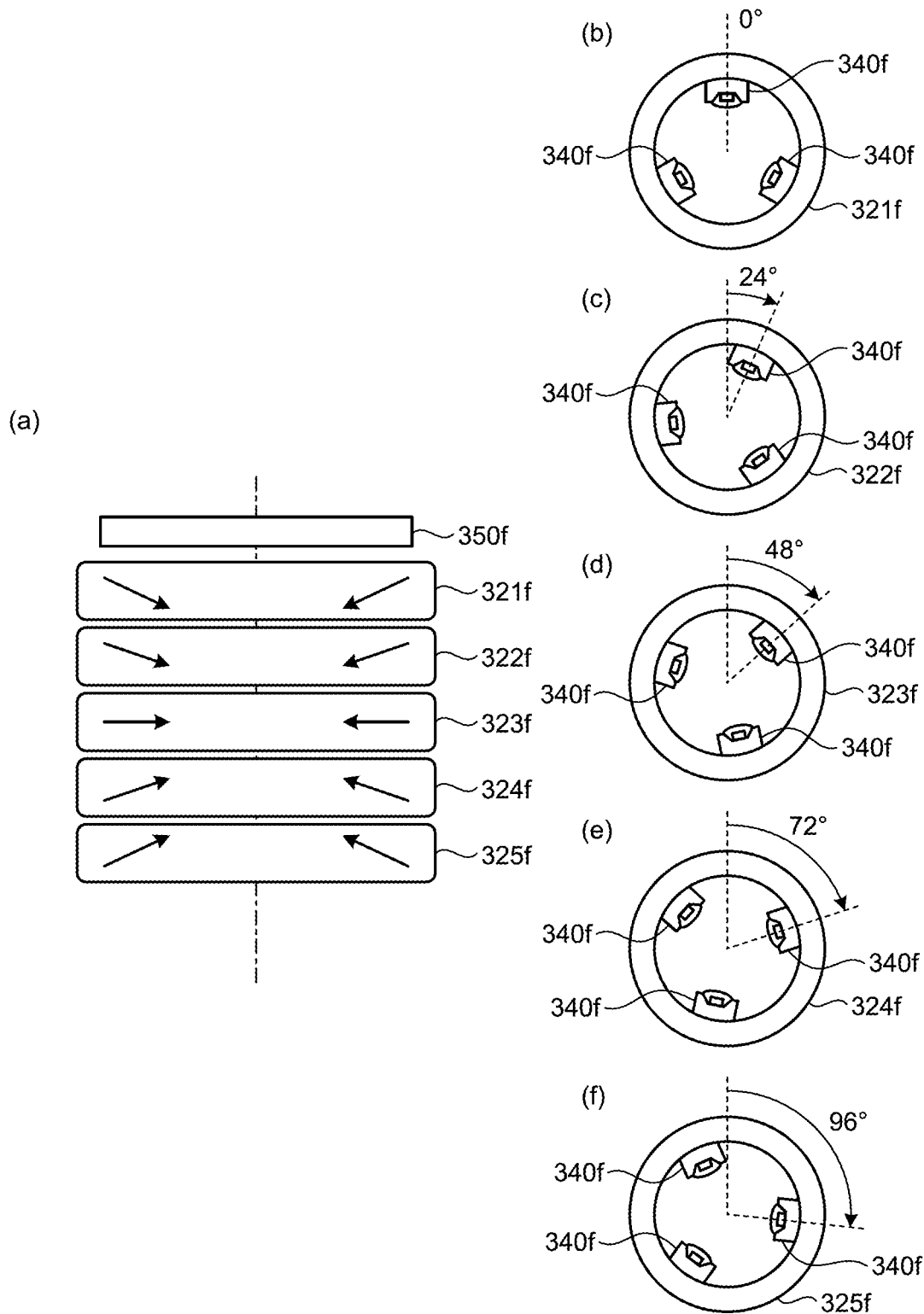
FIG. 7 is a diagram illustrating a configuration of ultraviolet irradiation units and semiconductor ultraviolet light emitting elements, according to Example 6.

FIG. 7 schematically illustrates ultraviolet irradiation units and semiconductor ultraviolet light emitting elements, according to Example 6. The ultraviolet irradiation units according to Example 6 are also applicable as the plural ultraviolet irradiation units 320 in the above described ultraviolet irradiation device 300.

As illustrated in FIG. 7, the ultraviolet irradiation units according to Example 6 include first to fifth ultraviolet irradiation units 321f, 322f, 323f, 324f, and 325f that irradiate ultraviolet curable resin with ultraviolet light, and a deep ultraviolet irradiation unit 350f that performs irradiation with deep ultraviolet light. As illustrated in FIG. 7(b) to FIG. 7(f), the first to fifth ultraviolet irradiation units 321f to 325f are units of the same type, each unit having three semiconductor ultraviolet light emitting elements 340f arranged on the same circle, and as illustrated in FIG. 7(a), these first to fifth ultraviolet irradiation units 321f to 325f are arranged in the traveling direction of the optical fiber such that the optical fiber passes the centers of the circles. Further, the deep ultraviolet irradiation unit 350f is arranged upstream of (upper than, on the plane of paper) the first ultraviolet irradiation unit 321f relative to the travelling direction of the optical fiber. The deep ultraviolet irradiation unit 350f has the same configuration as the deep ultraviolet irradiation unit 350d according to Example 4.

Similarly to Example 4, arrangement of the deep ultraviolet irradiation unit 350f upstream of the first ultraviolet irradiation unit 321f contributes to improvement in quality of the surface, through curing of ultraviolet curable resin in a layer closer to the surface that more easily reacts with oxygen, first.

The ultraviolet irradiation units according to Example 6 may be considered as units having the deep ultraviolet irradiation unit 350*f* in addition to the ultraviolet irradiation units according to Example 3. Therefore, the ultraviolet irradiation units according to Example 6 provide substantially the same functions and effects of the ultraviolet irradiation units according to Example 3.

Comparative Example

Figure 8:
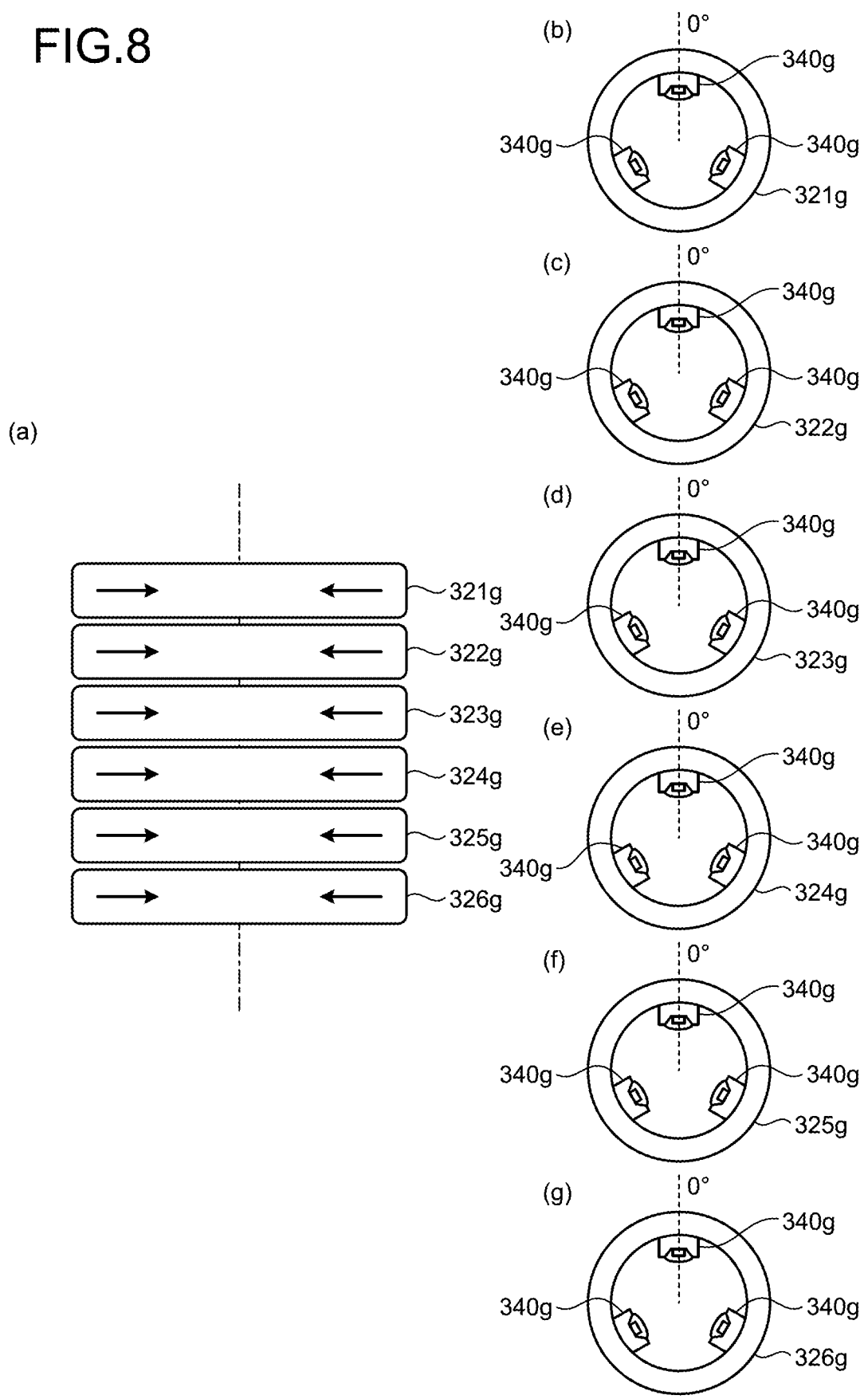
FIG. 8 is a diagram illustrating a configuration of ultraviolet irradiation units and semiconductor ultraviolet light emitting elements, according to a comparative example.

FIG. 8 illustrates ultraviolet irradiation units and semiconductor ultraviolet light emitting elements, according to a comparative example. This comparative example is prepared for verification experiments described later, in order to verify effects of the present disclosure. The ultraviolet irradiation units according to the comparative example are also applicable as the plural ultraviolet irradiation units 320 in the above described ultraviolet irradiation device 300.

As illustrated in FIG. 8, the ultraviolet irradiation units according to the comparative example are formed of first to sixth ultraviolet irradiation units 321*g*, 322*g*, 323*g*, 324*g*, 325*g*, and 326*g* that irradiate ultraviolet curable resin with ultraviolet light. As illustrated in FIG. 8(*b*) to FIG. 8(*g*), the first to sixth ultraviolet irradiation units 321*g* to 326*g* are units of the same type, each unit having three semiconductor ultraviolet light emitting elements 340*g* arranged on the same circle, and as illustrated in FIG. 8(*a*), these first to sixth ultraviolet irradiation units 321*g* to 326*g* are arranged in the traveling direction of the optical fiber such that the optical fiber passes the centers of the circles.

Therefore, the configuration of the ultraviolet irradiation units and semiconductor ultraviolet light emitting elements according to the comparative example is about the same as the configuration of the ultraviolet irradiation units and semiconductor ultraviolet light emitting elements according to Example 1, but in this comparative example, as illustrated in FIG. 8(*b*) to FIG. 8(*g*), the first to sixth ultraviolet irradiation units 321*g* to 326*g* have the same arrangement of the semiconductor ultraviolet light emitting elements 340*g* with respect to their circumferential direction angles around an axis that is the traveling direction of the optical fiber. The semiconductor ultraviolet light emitting elements 340*g* included in the first to sixth ultraviolet irradiation units 321*g* to 326*g* emit ultraviolet light perpendicularly to the axis representing the traveling direction of the optical fiber.

Modified Example

In the ultraviolet irradiation units or the deep ultraviolet irradiation units described in Examples 1 to 6, the semiconductor ultraviolet light emitting elements are arranged in these units themselves. However, ultraviolet light emitted from an ultraviolet light source may be guided through an optical fiber or the like to a position from which the ultraviolet light is to be emitted toward the travelling optical fiber having ultraviolet curable resin thereon. When a plurality of so-configured ultraviolet light irradiation units are assembled into the ultraviolet irradiation unit 320 in a similar manner as the ultraviolet light irradiation units according to Examples 1 to 6, effects similar to those of Examples 1 to 6 are able to be achieved.

Verification Experiments

Table 1 below summarizes results of experiments for verification of effects of bare optical fiber manufacturing methods and ultraviolet irradiation devices, according to the embodiment of the present disclosure. The verification experiments of which results are listed in Table 1 were performed for verification of characteristics of bare optical fibers when the bare optical fibers were manufactured by use of ultraviolet irradiation devices, to which the configurations described in Examples 1 to 6 and the comparative example had been applied.

As a method of forming coatings around the optical fibers, a wet-on-dry method was adopted, and for facilitation of verification of the effects, the embodiment of the present disclosure was applied only to secondary layers. Further, a photopolymerization initiator used in ultraviolet curable resin of the secondary layers was Irgacure 184 (BASF Japan Co., Ltd.).

TABLE 1

|  |  | Example 1 | Example 2 | Example 3 | Example 4 | Example 5 | Example 6 | Comparative Example |
|---|---|---|---|---|---|---|---|---|
| Spiral Arrangement | | Yes | Yes | Yes | Yes | Yes | Yes | No |
| Number Of Elements | counts/unit | 3 | 4 | 3 | 3 | 4 | 3 | 3 |
| Condensing by Elements | | No | No | Yes | No | No | Yes | No |
| deep-UV | | No | No | No | Yes | Yes | Yes | No |
| Number Of Units | counts | 6 | 4 | 5 | 6 | 4 | 5 | 6 |
| Power Consumption Reduction Rate | % | 0 | 12 | 20 | 0 | 12 | 20 | — |
| Presence of Undulation | | Not present | Not present | Not present | Not present | Not present | Not present | Present |
| knot test | N | 0.095 | 0.084 | 0.088 | 0.051 | 0.042 | 0.035 | 0.091 |
| Cable Loss | dB/km | 0.226 | 0.221 | 0.216 | 0.194 | 0.190 | 0.187 | 0.228 |
| 2.5% Modulus | MPa | 1011 | 964 | 998 | 1056 | 978 | 1007 | 789 |

As illustrated in Table 1, in the verification experiments, reduction rates of power consumption, presence of undulation, knot tests, cable losses, and 2.5% moduli were compared. Reduction rates of power consumption mean reduction rates of power consumption as compared to the comparative example. Presence of undulation is determined by measuring lengths of a same bare optical fiber manufactured, in a state where tension is applied and in a state where tension is not applied. When a length of a bare optical fiber measured with tension applied thereto is 30 m and then reduced by 5 cm or more when the tension is released, undulation is determined to be present. The tension is applied when a bare optical fiber is reeled out from a bobbin, and 50 g is used.

Figure 9:
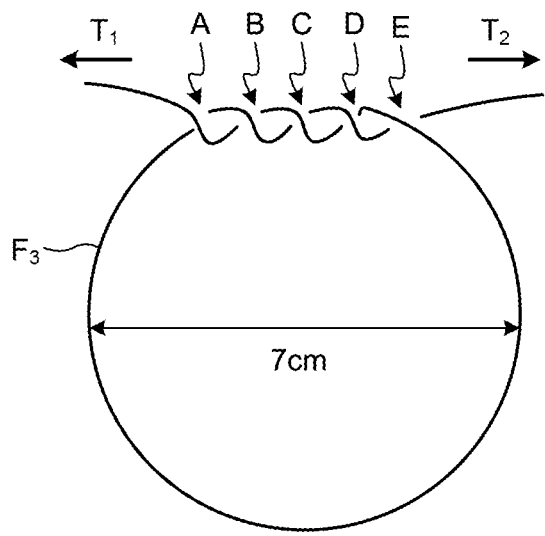
FIG. 9 is a schematic diagram illustrating an outline of a knot test implemented.

A knot test is evaluation of kinetic friction of a surface of a bare optical fiber. FIG. 9 is a schematic diagram illustrating an outline of a knot test implemented. In this measurement method, as illustrated in FIG. 9, a single loop having a diameter of about 7 cm is made with a bare optical fiber $F_3$ manufactured, and both end portions of the bare optical fiber $F_3$ are knotted or twisted five times, so that the bare optical fiber $F_3$ contacts itself at five points A to E. Then, both ends of this optical fiber are pulled at a speed of 5 mm/minute by a tension tester. Loads [N] measured thereby are used as results thereof.

Figure 10:
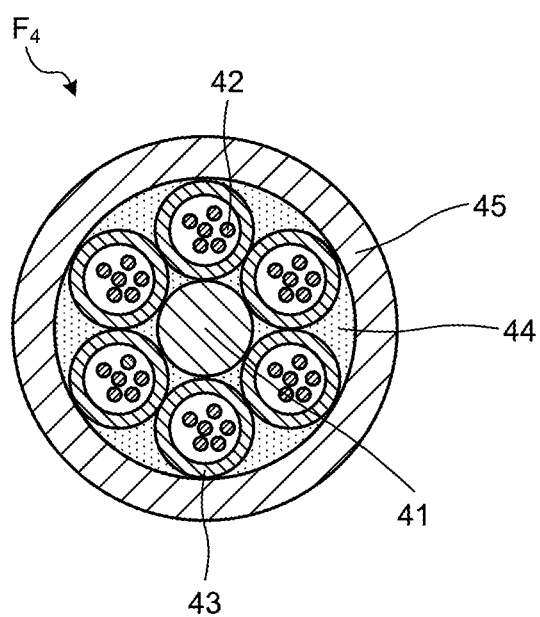
FIG. 10 is a sectional view illustrating a structure of a loose tube type optical fiber cable.

Further, a cable loss is a loss related to transmission of light of a wavelength of 1.55 μm in a loose tube type optical fiber cable made by use of a bare optical fiber, and a permissible range of cable loss is 0.230 dB/km or less. FIG. 10 is a sectional view illustrating a structure of a loose tube type optical fiber cable. A cable loss was measured by use of this loose tube type optical fiber cable. As illustrated in FIG. 10, a loose tube type optical fiber cable $F_4$ is formed of a tension member 41, colored and coated optical fibers 42, plural loose tubes 43, jelly 44, and a sheath 45. The tension member 41 is made of metal or plastic. The plural loose tubes 43 made of metal or plastic are provided on a cylindrical lateral surface of the tension member 41, with the colored and coated optical fibers 42 inserted through the loose tubes 43. These loose tubes 43 are surrounded by the sheath 45 made of plastic, and void spaces within the sheath 45 are filled with the jelly 44.

Values of 2.5% modulus (elastic modulus) are measured as follows. First, bare optical fibers manufactured by manufacturing methods using ultraviolet irradiation devices, to which the configurations according to Examples 1 to 6 and the comparative example are applied, are immersed in liquid nitrogen, glass fibers are drawn out therefrom by use of a coating removing tool at a liquid nitrogen temperature, and coating layers remain tubular. These tubular optical fiber coating layers having a length of 50 mm are prepared as a sample, 2.5% moduli are measured at a gauge length of 25 mm in conformance to JIS K 7161.

As understood from Table 1, the bare optical fibers manufactured by use of the ultraviolet irradiation devices, to which the configurations according to Examples 1 to 6 are applied, have no undulation, but the bare optical fiber manufactured by use of the ultraviolet irradiation device, to which the configuration according to the comparative example is applied, has undulation. This indicates that the circumferential surface of the ultraviolet curable resin applied onto the optical fiber is uniformly irradiated with the ultraviolet light in the ultraviolet irradiation devices, to which the configurations according to Examples 1 to 6 are applied, and thus satisfactory coatings are formed.

Further, as understood from Table 1, the bare optical fibers manufactured by use of the ultraviolet irradiation devices, to which the configurations according to Examples 4 to 6 are applied, have significantly improved measurement results for their knot tests. The results indicate that in the ultraviolet irradiation devices, to which the configurations according to Examples 4 to 6 are applied, quality of surfaces of the coatings is improved by curing first the shallower part of the ultraviolet curable resin by use of the deep ultraviolet irradiation units.

Further, as understood from Table 1, the bare optical fibers manufactured by use of the ultraviolet irradiation devices, to which the configurations according to Examples 1 to 6 are applied, have satisfactory values for cable loss.

Further, as understood from Table 1, the bare optical fibers manufactured by use of the ultraviolet irradiation devices, to which the configurations according to Examples 1 to 6 are applied, are higher in 2.5% modulus than the bare optical fiber manufactured by use of the ultraviolet irradiation device, to which the configuration according to the comparative example is applied. This indicates that in the ultraviolet irradiation devices, to which the configurations according to Examples 1 to 6 are applied, ultraviolet curable resin is sufficiently irradiated with ultraviolet light and satisfactory coatings are formed.

As understood from Table 1, power consumptions of the ultraviolet irradiation devices, to which the configurations according to Examples 2, 3, 5, and 6 are applied, are less than that of the ultraviolet irradiation device, to which the configuration according to the comparative example is applied. This is because the number of semiconductor ultraviolet light emitting elements used in each of the ultraviolet irradiation devices, to which the configurations according to Examples 2, 3, 5, and 6 are applied, is less than the number of semiconductor ultraviolet light emitting elements used in the ultraviolet irradiation device, to which the configuration according to the comparative example is applied. In the ultraviolet irradiation devices, to which the configurations according to Examples 5 and 6 are applied, semiconductor ultraviolet light emitting elements that emit deep ultraviolet light are also used, but since power consumptions of the semiconductor ultraviolet light emitting elements that emit deep ultraviolet light are less than those of normal semiconductor ultraviolet light emitting elements, their influence is negligibly small.

The above described results mean that the ultraviolet irradiation devices, to which the configurations according to Examples 2, 3, 5, and 6 are applied, are capable of reducing power consumptions in the ultraviolet irradiation devices while maintaining their performance related to the presence of undulation, knot tests, cable losses, and the like.

Results of the verification experiments related to advantages of the configurations according to Examples 3 and 6 will now be described. In each of the configurations according to Examples 3 and 6, the semiconductor ultraviolet light emitting elements are arranged to emit ultraviolet light toward the vicinity of a single point on the axis representing the traveling direction of the optical fiber. How this arrangement contributes to curing of the coating will be described.

Figure 11:
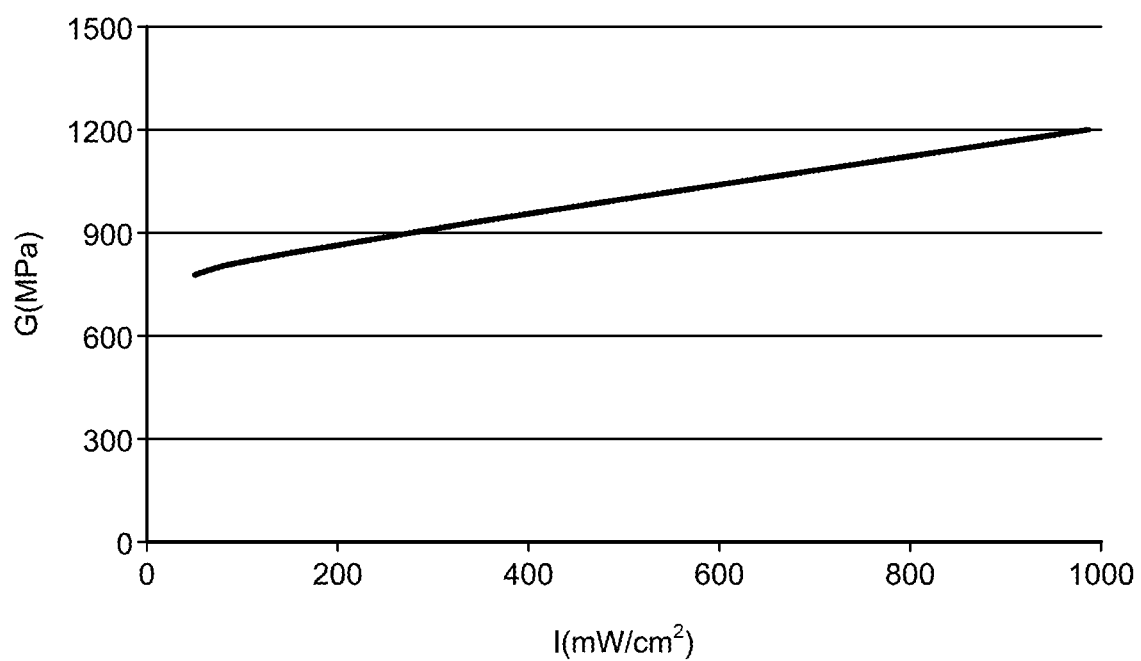
FIG. 11 is a diagram illustrating a graph representing a relation between: illuminance of ultraviolet light that ultraviolet curable resin is irradiated with; and 2.5% modulus.

FIG. 11 is a graph representing a relationship between illuminance (I) of ultraviolet light that ultraviolet curable resin is irradiated with and 2.5% modulus (G). Measurement results illustrated in FIG. 11 are obtained by the following measurement.

A base material made of quartz glass was prepared, and was spin-coated with an ultraviolet curable resin, which was the same resin as that used as the second layer in the above verification experiments, in a thickness of 50 μm. The base material, onto which the ultraviolet curable resin for the secondary layer was applied, was placed in a purge box, which was then made to have a nitrogen atmosphere, and the resin was cured by irradiation with ultraviolet light (365 nm), with illuminance and speed being adjusted in a conveyor type ultraviolet irradiation device such that a predetermined amount of accumulated light was obtained.

The cured ultraviolet curable resin for the secondary layer was peeled off from the base material, and cut into a strip having a width of 6 mm and a length of 50 mm or more, as a sample. A 2.5% modulus (elastic modulus) of this sample was measured at a gauge length of 25 mm in conformance to JIS K 7161.

As understood from the graph illustrated in FIG. 11, the higher the illuminance of ultraviolet light that the ultraviolet curable resin is irradiated with, the higher the 2.5% modulus is. Therefore, for an ultraviolet irradiation device, a configuration enabling increase in illuminance of ultraviolet light emitted to an ultraviolet curable resin is preferably adopted for formation of a better coating. In each of the configurations of the ultraviolet irradiation devices according to Examples 3 and 6, the semiconductor ultraviolet light emitting elements are configured to emit ultraviolet light toward the vicinity of a single point on the axis representing the traveling direction of the optical fiber, and thus illuminance of ultraviolet light emitted to the ultraviolet curable resin is increased, and a better coating is able to be formed.

The embodiment of the present disclosure has been specifically described above, but the present disclosure is not limited to the above described embodiment, and various modifications based on technical ideas of the present disclosure are possible. For example, in each of Examples 1 to 6 described above, all of the ultraviolet irradiation units have different arrangements with respect to their circumferential direction angles around the axis that is the traveling direction of the optical fiber, but as long as at least two of the ultraviolet irradiation units have different arrangements with respect to their circumferential direction angles around the axis that is the traveling direction of the optical fiber, a coating better than that of the comparative example is able to be formed.

Further, in each of Examples 1 to 6 described above, the semiconductor ultraviolet light emitting elements included in the ultraviolet irradiation units are arranged in a spiral around the axis that is the traveling direction of the optical fiber, but not necessarily arranged in a spiral, and the semiconductor ultraviolet light emitting elements may be arranged differently in an irregular manner with respect to the circumferential direction angles around the axis that is the traveling direction of the optical fiber.

Further, although verification experiments focused only on the secondary layers were performed as the above described verification experiments for Examples 1 to 6, the embodiment of the present disclosure may be applied onto primary layers.

A bare optical fiber manufacturing method and an ultraviolet irradiation device, according to the present disclosure, have an effect of enabling ultraviolet curable resin to be cured sufficiently even if ultraviolet light of a single wavelength or a narrow wavelength bandwidth is used.

What is claimed is:

1. A bare optical fiber manufacturing method comprising:
applying an ultraviolet curable resin applied around an optical fiber; and
irradiating the ultraviolet curable resin with ultraviolet light emitted from semiconductor ultraviolet light emitting elements wherein plural of the semiconductor light emitting elements are arranged in plural ultraviolet irradiation units;
wherein each of the plural ultraviolet irradiation units including a circle which has an open space between the circle of an adjacent ultraviolet irradiation unit in a length direction of the optical fiber, wherein each of the plural ultraviolet irradiation units includes the semiconductor light emitting elements arranged around the circle, with each circle having a center on a central axis and each circle having a circumference about the central axis; each of the plurality ultraviolet irradiation units being arranged relative to the plurality of the ultraviolet irradiation units in the length direction of the optical fiber such that the optical fiber passes longitudinally through an inside of the ultraviolet irradiation unit along the center of each circle of the plural ultraviolet irradiation units, wherein a first ultraviolet irradiation unit is arranged to have the semiconductor ultraviolet light emitting elements at different positions on the circumference of each circle around the central axis relative to the central axis that extends in a traveling direction of the optical fiber in comparison that positions of the semiconductor ultraviolet light emitting elements on the circumference around the central axis of a second ultraviolet irradiation unit, wherein semiconductor ultraviolet light emitting elements in the first and second ultraviolet irradiation units are rotationally deviated from an angularly adjacent semiconductor ultraviolet light emitting element in a same ultraviolet irradiation unit, and the semiconductor ultraviolet light emitting elements included in the plural ultraviolet irradiation units are installed at an incline in each of the plural ultraviolet irradiation units to emit the ultraviolet light toward a vicinity of a single point on the central axis extending lengthwise in the length direction of the optical fiber; and the positions of the semiconductor ultraviolet light emitting elements form a cylindrical surface with the central axis of the plural ultraviolet irradiation units and along which the optical fiber travels.

2. The bare optical fiber manufacturing method according to claim 1, wherein the semiconductor ultraviolet light emitting elements further include a deep ultraviolet irradiation unit that emits deep ultraviolet light, the deep ultraviolet irradiation unit being upstream of the plural ultraviolet irradiation units in the traveling direction of the optical fiber, and the ultraviolet curable resin applied around the optical fiber is irradiated with the ultraviolet light after being irradiated with the deep ultraviolet light.

\* \* \* \* \*